United States Patent [19]

Dieringer

[11] Patent Number: 5,195,994
[45] Date of Patent: Mar. 23, 1993

[54] COUPLING FOR JOINING FLEXIBLE TUBING FOR MEDICAL PURPOSES

[76] Inventor: Franz A. Dieringer, Prinz Eugenstrasse 18, A-1040 Vienna, Austria

[21] Appl. No.: 573,018
[22] PCT Filed: Jan. 19, 1990
[86] PCT No.: PCT/AT90/00008
    § 371 Date: Nov. 7, 1990
    § 102(e) Date: Nov. 7, 1990
[87] PCT Pub. No.: WO90/07953
    PCT Pub. Date: Jul. 26, 1990

[30] Foreign Application Priority Data

Jan. 19, 1989 [AT] Austria .................. 104/89

[51] Int. Cl.$^5$ .................................. A61M 25/00
[52] U.S. Cl. ........................... 604/283; 604/326; 604/256; 604/905; 128/912
[58] Field of Search ............... 604/236–237, 604/280, 283, 164, 905, 326, 256, 244, 249, 167, 166, 170, 246, 748; 128/912, 766; 285/3/4

[56] References Cited

U.S. PATENT DOCUMENTS

| 4,334,551 | 6/1982 | Pfister | 137/614,03 |
| 4,610,469 | 9/1986 | Wolff-Mooij | 604/905 |
| 4,636,204 | 1/1987 | Chrsitopherson et al. | 604/905 |
| 4,655,762 | 4/1987 | Rogers | 128/912 |
| 4,752,292 | 6/1988 | Lopez et al. | |
| 4,781,702 | 11/1988 | Herrli | |

FOREIGN PATENT DOCUMENTS 386523   9/1988 Austria .
0080379  6/1983 European Pat. Off. .
0116986  8/1984 European Pat. Off. .

Primary Examiner—John D. Yasko
Assistant Examiner—Ronald Stright, Jr.
Attorney, Agent, or Firm—Jacobson, Price, Holman & Stern

[57] ABSTRACT

A coupling for connecting hose lines for medical purposes including a first coupling member (1) having supported therein an axially shiftable hollow plug (2) with a tapered connector (16) for connecting thereto a first hose length and extending in its operating position through a sponge member (9) soaked with a disinfectant and capable of being pierced through a diaphragm (11) for coupling with a second coupling member (5), both coupling members (1, 5) being releasably connected together. Hollow plug (2) consists of outer and inner parts (3, 4) concentrically and telescopically arranged relative to each other so that both parts (3, 4) of the plug (2) are relatively axially and rotatably shiftable whereby a transverse flow passage (19) in outer part (3) is closed by inner part (4) or communicates with channel grooves (20) in the inner part to facilitate flow through the coupling.

20 Claims, 3 Drawing Sheets

COUPLING FOR JOINING FLEXIBLE TUBING FOR MEDICAL PURPOSES

BACKGROUND OF THE INVENTION

1. Field of the Invention

The invention refers to a coupling for connecting hose conduits for medical purposes, and mole particularly to such a coupling including a first coupling member having supported therein an axially shiftable hollow plug for connecting thereto a first hose length and extending in its operating position through a sponge member capable of being soaked with a disinfectant and being capable of being pierced through a diaphragm for coupling to a second hose length, the diaphragm being connected with a second coupling member and both coupling members being releasably connected one with the other.

2. Description of the Prior Art

A device of the initially mentioned type has become known from German Patent Document AT-PS 386 523. In the known sterile connection, a plug is supported within a coupling member for being axially shiftable, and, when axially shifting the plug, the free end of the plug located remote from the hose connection is moved through elastically deformable insects, in particular bodies of foamed material, being impregnated with a disinfectant. In the known arrangement there is used in an advantageous manner a multipart insert member consisting of foamed material and receiving the disinfectant, so that it is possible to permanently make available within this coupling member a minimum amount of disinfectant and to replenish the required amount of disinfectant by means of the second removable body of foamed material when using the device several times. In this case, the bodies of foamed material have an opening being concentric relative to the axis of the plug and are, when shifting the plug in the axial direction, pressed against the outer surface of the plug under elastic compression. In this known arrangement, the second coupling member to be coupled with the first coupling member has the sole function to close in a sterile manner the equipment, such as for example in fusion bottles or the like, connected to said coupling member, for which purpose there is connected with the second coupling member a perforable diaphragm.

The hose line connected with the plug has, for example, been directly connected with the patient via a catheter and could remain in permanent connection with such a catheter when in fusion bottles,, bags or the like had to be interchanged. For such an interchange it was only necessary to move the plug back into its retracted position to make sure that any risk of infection is reduced when interchanging the infusion equipment or the like. The second coupling member could be brought into a conductive connection with the infusion equipment, in particular infusion bottles or the like, and when again extending the shiftable plug an open flow section of the hose conduit could be obtained with a minimum risk of contamination. In the known arrangement, the hose conduit leading to the patient was never closed. In contrast thereto, the openings, through which the plug has been shifted and via which the flow connection with the hose length connected to the second coupling member had been established, had, in the retracted position of the plug, their ends within the sponge member soaked with the disinfectant, which resulted, on the one hand, in the risk of sucking disinfectant from this sponge member into the conduit leading to the patient and, on the other hand, resulted in the possibility that in case of a corresponding pressure difference body fluids could be pressed into the sponge member.

SUMMARY OF THE INVENTION

It is an object of the invention to provide a device of the initially mentioned type for providing the possibility to tightly close the conduit leading to the patient simultaneously with the retracting movement of the plug being effected when interchanging the infusion equipment. For solving this task, the arrangement according to the invention consists, in principle, in that the hollow plug consists of two parts concentrically arranged one relative to the other, noting that both parts of the plug are adapted for being axially shiftable one relative to the other or in common and that, in encased position of the parts of the plug, the outflow opening of the plug is closable. On account of the plug being a bipartite plug, there is provided the possibility to close the conduit in its part connected to the plug either by relative rotation of both plug parts one against the other or by axially shifting one plug part relative to the other plug part. In this case, it is sufficient to design the corresponding connecting bores such that they are in mutual alignment in the operating position and thus provide for an open flow through the conduit and that they slide, in the retracted position, one past the other in a manner providing a tight seal. This can, in a simple manner, be achieved if the outer part of the plug is supported for being shifted together with the inner part of the plug and is supported on the inner part of the plug for being rotatable. In such an arrangement, an open connection between the inner plug part and the outer plug part can be obtained in a predetermined rotated position, to the latter whereas such an open connection can be interrupted in a rotated position corresponding to the position for retracting the plug. This is in a simple manner achieved if the inner part of the plug has channels or grooves extending in axial direction and the outer part has radial perforations opening into the channels or grooves of the inner part in one relative rotated position between the outer part and the inner part. Such channels or grooves extending in the longitudinal direction of the inner part of the plug form axially extending flow channels which can, in dependence on the rotated position of the outer part of the plug, be brought in aligned position with the corresponding perforations or, respectively, radial flow passages of the outer part of the plug, whereas the radial flow passages of the outer part of the plug can be covered by the material of the inner plug in a non-aligned rotated position at the grooves and perforations. If one plug part is axially shiftable relative to the other plug part, there must be provided a corresponding circumferential seal and there must be reached, when shifting the outer part of the plug over the inner part of the plug, an end position in which the flow passages of the outer part are closed by means of sealing elements provided on the circumference of the inner part of the plug.

For the purpose of further increasing the safety against contamination and in particular also the safety against dragging disinfectant into the blood path, the arrangement is advantageously such that an absorbing insert, in particular an annular disc consisting of foamed material, is provided as a stripper disc within the second coupling member carrying the perforable diaphragm.

Such a stripper disc absorbs any disinfectant, present on the outer surface of the plug, and in consideration of the circumstance that this stripper disc is supported in the second coupling member, it is made sure that when interchanging the infusion equipment always fresh stripper discs are used together with the diaphragm to be perforated. In this case, the arrangement can in an advantageous manner be such that the perforable diaphragm or diaphragms, the stripper disc as well as, optionally, the sealing disc are arranged within a common constructional part which can be locked with the second coupling member, to assure that the stripper disc and the diaphragm are interchanged in common.

In the known construction of the coupling, the remaining residual volume of air contained, if at all, was comparatively small, but on account of the construction of the known constructional parts small residual amounts of air remain within the conduit and subsequently enter the blood path via the tubular plug together with the fluid supplied via the hose line. For the purpose of reliably preventing any dragging of such residual amounts of air into the blood path, the arrangement in the invention is advantageously such that the second coupling member has a connecting piece for the second hose length eccentrically arranged relative to the shifting path of the plug and has an air venting opening coaxially arranged relative to the shifting path of the plug adapted to be closed by the plug in the coupled position. When connecting a new infusion bottle to such a second coupling member, the residual air volume can first be forced out through the air venting opening, and the central air venting opening can be tightly closed by the plug itself in the operating position of the plug. For this purpose, the arrangement is advantageously such that the front end of the outer part of the plug carries an axial sealing protrusion tightly entering into the air venting opening of the second coupling member in the coupled position. For the purpose of facilitating ventilation of the fluid when effecting coupling to the second coupling member and, in particular, for preventing the fluid from soaking the stripper disc provided on the second coupling member and thus from making the stripper disc inoperative, the arrangement is advantageously such that the second coupling member has, in addition to the perforable diaphragm located opposite the connecting piece for the second hose length and in addition to the stripper disc, a further perforable diaphragm or a sealing disc separating the space, into which the connection for the second hose length, opens from the stripper disc. In this manner, the stripper disc is maintained in a dry condition and is maintained absorbable for the disinfectant adhering, if at all, on the outer surface of the plug.

For the purpose of assuring reliable connecting of the parts of the plug, the arrangement is advantageously such that the inner part of the plug has, at its end located opposite the outflow openings of the outer part, claws embracing a base disc of the outer part. Such type of connection between both parts of the plug reliably provides for relative rotation of the outer part of the plug on the inner part of the plug without detracting from the stability of the connection in the axial direction. For the purpose of simultaneously obtaining a great sealing effect, there can be provided in such an arrangement a corresponding seal within the area of this force-locking connection against axial shifting movement, for which purpose the arrangement is advantageously such that the inner part of the plug has, within the area of the claws, a conical sealing surface for engagement with a hollow-conical cooperating surface provided within or in proximity of the base part of the outer part of the plug. In this manner, there can be produced in a simple manner a bipartite plug of high precision, good sealing properties and facilitated rotatability of the outer part of the plug relative to the inner part of the plug.

When using conical sealing surfaces, there exists, however, on frequent use the risk of jamming of the conical sealing surfaces, because primarily synthetic plastics materials are used for the inner part as well as for the outer part. Jamming results in an increase of the force to be exerted for rotating the outer part on the inner part of the plug, and for this reason the arrangement is advantageously such that the outer part of the plug is supported on the cone of the inner part with interposition of an annular seal, in particular a lip seal. In this manner, there is assured over long operating periods an exact seal as well as ease of rotation.

For the purpose of providing the possibility of rotating the outer part of the plug on the inner part of the plug, the arrangement is advantageously such that the outer part has a radial actuating protrusion for the manipulating rotating movement around the axis of the inner part, the radial actuating protrusion being guided within a guide slot of the first coupling member for shafting in the axial direction and in the circumferential direction of the first coupling member in the predetermined axially shifted position. The slot-like guide means simultaneously assures that the locked position, i.e. the rotated position of the outer part of the plug relative to its inner part intended for obstructing the free flow through the exit openings of the outer part of the plug, is positively reached when retracting the plug. A reliable closure of the conduit connected with the patient is thus automatically obtained when retracting the plug for the purpose of interchanging the infusion equipment.

BRIEF DESCRIPTION OF THE DRAWING

In the following, the invention is further explained with reference to an embodiment schematically shown in the drawing wherein.

DETAILED DESCRIPTION OF THE PREFERRED EMBODIMENT

Figure 1:
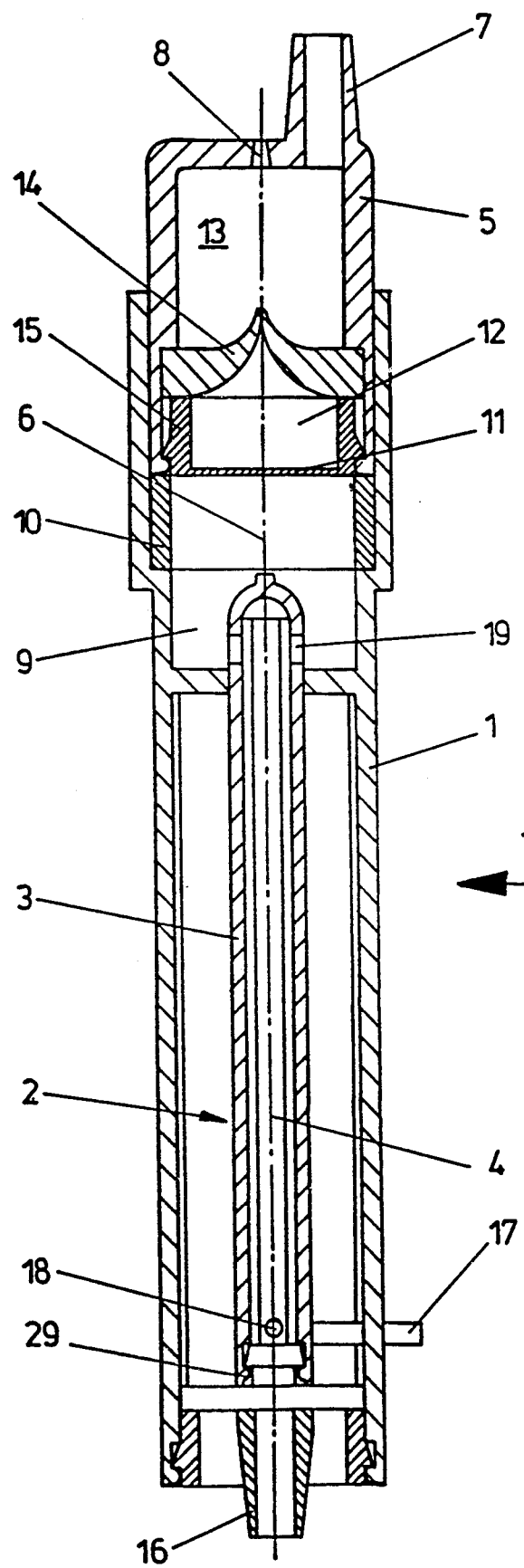
FIG. 1 is a schematic axial cross-sectional view of the inventive coupling.

In FIG. 1 there is shown a first coupling member 1 having a plug 2 being shiftable in the axial direction, noting that this plug 2 consists of an outer part 3 and of an inner part 4. A second coupling member 5 is connected to the first coupling member 1 and has a connecting piece 7 located eccentrically relative to the axis 6 of the plug or, respectively, the shifting path of the plug and having connected thereto a hose line leading to an infusion equipment. Centrally and on axis 6 there is provided on the second coupling member 5 an air ventilation bore 8. When shifting the plug 2 in the axial direction, the plug 2 is first moved through a first insert member of absorbing material permanently soaked by a disinfectant. proceeding in the axial direction, there is provided a second interchangeable absorbing insert member 10, in which the disinfectant can be replenished for assuring a reliable disinfection. Within the second coupling part 5, there is provided a perforable diaphragm 11 as well as a further absorbing insert member 12 in the manner of a stripping disc which wipes off and absorbs any material adhering on the outer surface of the plug 2.

When connecting an infusion bottle to the connecting piece 7, air ventilation can be achieved by introducing into the space 13 the entering fluid until the fluid flows out of the air ventilating bore 8. For the purpose of making sure that the stripping insert member 12 does not come, during such scavenging procedure for removing residual air, in contact with the fluid and is thus not soaked with fluid and thus maintains its absorbing capacity, there is provided a sealing insert 14, which forms a central closure means like a lip seal. In place of such a sealing insert 14 there can of course be provided a further perforable diaphragm being analog to the diaphragm 11, noting that the diaphragm 11, the stripper disc 12 as well as the sealing disc 14 are held by a common constructional part 15 which can be locked with the second coupling member 5.

For the purpose of assuring a tight closure of the conduit leading to the patient and being connected to the plug via the connecting piece 16 in the retracted position of the plug shown in FIG. 1, the outer part 3 of the plug 2 is provided with a radial actuating protrusion 17 extending through a guiding slot 27 in the wall of the first coupling member 1. The inner plug part 4 has at least one radial bore 18 in connection with the axial opening in connecting piece 16 and channels 20 in inner part 4. Radial passages 19 in outer part 3 are tightly engaged against the outer surface of inner part 4 of the plug 2 in the rotated position shown in FIG. 1, so that the radial passages 19 of the outer part 3 of the plug are, in the position shown in FIG. 1, sealed against the radial bore 18 of the inner part 4. This is further made clear in the FIGS. 2 and 3.

Figure 2:
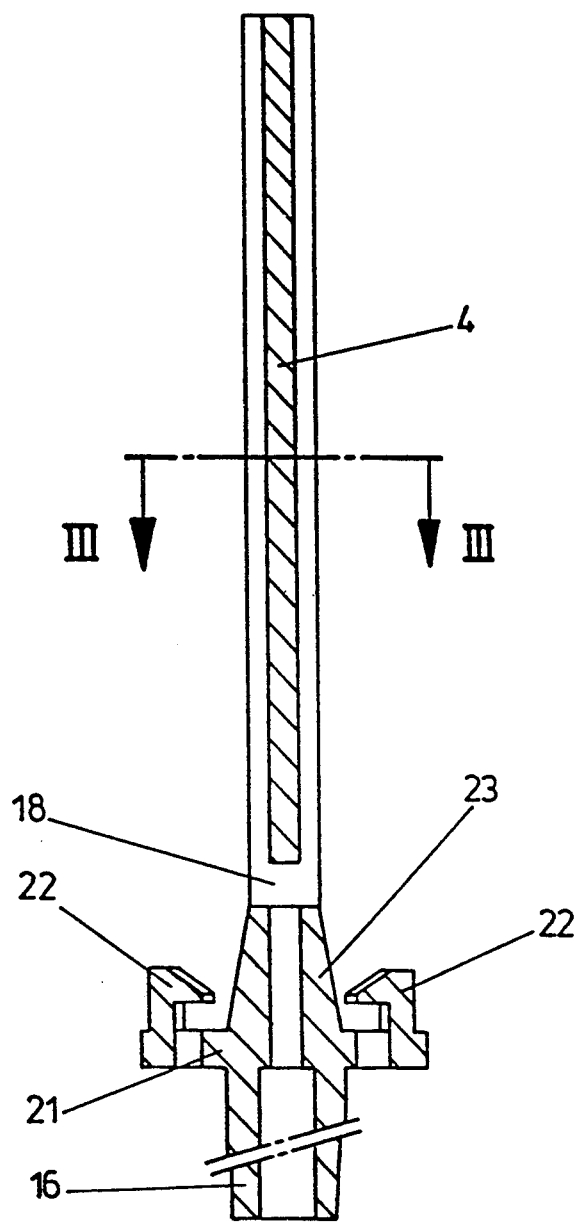
FIG. 2 is an enlarged cross-sectional view of the inner part of the plug of a device according to FIG. 1.
Figure 3:
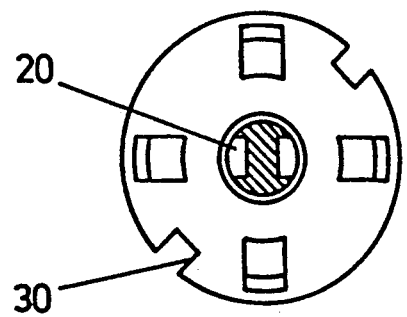
FIG. 3 is a cross-sectional view taken along lien III-—III of FIG. 2.

In FIGS. 2 and 3, the inner part 4 of the bipartite plug 2 is shown in an enlarged scale. The inner plug 4 has, as is shown in FIG. 3, channels 20 extending in the axial direction and adapted to be brought into alignment with the radial passages 19 of the outer part 3 of the plug in a predetermined relative rotated position. The inner part 4 of the plug is connected with a base member 21 provided with claws 22 for locking with the outer part 3 of the plug 2. The connecting piece 16 of the conduit leading to the patient opens, via the base member 21, into the radial channels 18 of the plug, the radial channels again opening into the axially extending space delimited by the channels 20 of the inner part of the plug 4 and the inner wall of the outer part 3 of the plug. The base member is further provided with a conical sealing surface 23 which, after putting the outer part of the plug into a rest position is secured against axial shifting movement by the claws 22 of the base member 21, forming a sealing surface relative to the outer part 3 of the plug.

Figure 4:
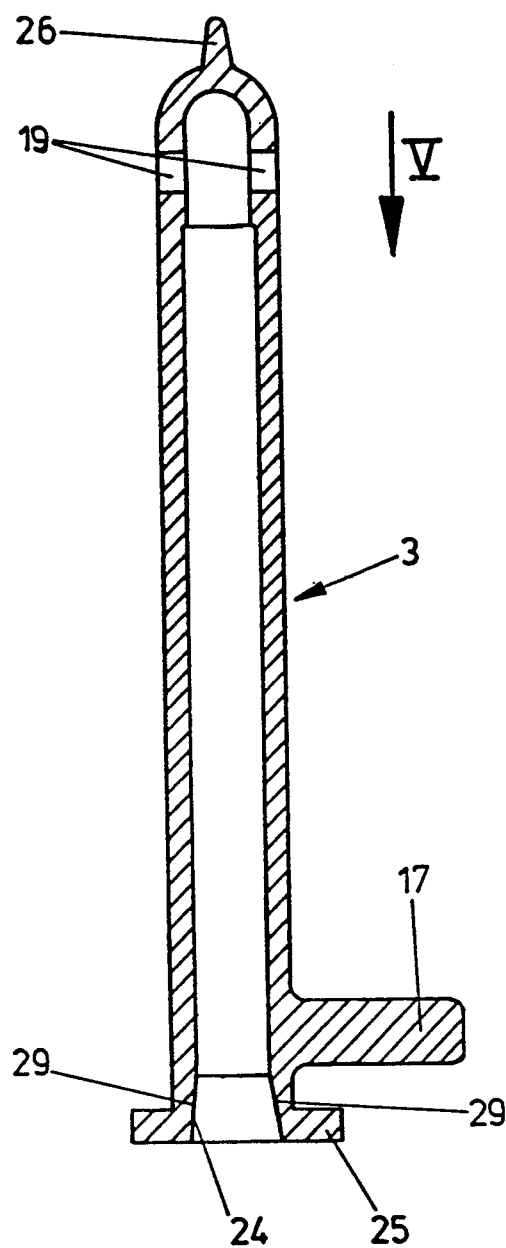
FIG. 4 is an axial cross-sectional view through the outer part of the plug.
Figure 5:
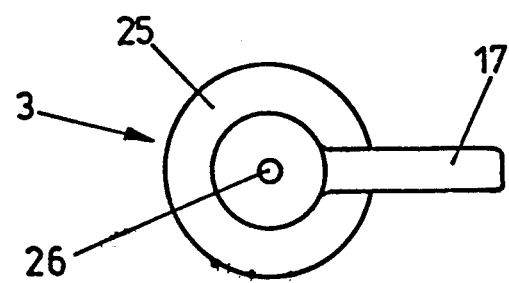
FIG. 5 is a top plan view in direction of the arrow V of FIG. 4.

In the representation according to FIGS. 4 and 5, the outer part 3 of the plug is shown in an enlarged scale, noting that there are again shown the radial bores 19, via which fluid can be introduced into the conduit leading to the patient. For this purpose there must, however, first be perforated diaphragm 11 of the second coupling member 5 and the plug must first be shifted in the axial direction and subsequently be rotated by means of the radial actuating protrusion 17 for the purpose of establishing the open connection between the radial bores 19 and the axially extending channels 20 of the inner plug. The outer part 3 of the bipartite plug has on its base member again conical sealing surfaces 24 cooperating with the conical sealing surfaces 23 of the inner plug in a sealing manner when put onto the inner part 4 of the plug. Within the same area, the outer part 3 of the plug carries a flange 25 embraced in a locking manner by the claws 22 of the inner part 4, so that relative swivellability is reliably maintained but axial separation of the outer part 3 from the inner part 4 is not possible without special measure.

The front end of the outer part 3 of the plug 2 has a sealing protrusion 26 which in the end position of the shifting path of the plug 2 is inserted into the air ventilating opening 8 of the second coupling member 5 and thus tightly closes that opening.

Figure 6:
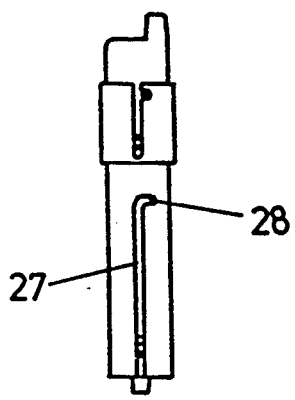
FIG. 6 is, in a reduced scale, a side elevational view in direction of the arrow VI of FIG. 1, which shows the guide slot for the relative rotation of the outer part of the plug on the inner part of the plug.

The guiding slot for the radial actuating protrusion 17 is clearly shown in the representation according to FIG. 6 as guiding groove 27 extending in a first partial range in the axial direction of the first coupling member 1. After having reached the end position of the plug, in which position the tip of the outer part 3 cooperates via the sealing protrusion 26 with the air ventilating opening 8, the radial actuating protrusion can be moved in the circumferential direction along the last oblique partial range 28 of the guiding groove, whereby the radial bores 19 of the outer part 3 are swivelled into an aligned position with the axial channels 20 of the inner plug 4 and the open connection between the connecting piece 7 of the coupling member 5 and the connecting piece 16 of the plug 2 is established. Simultaneously, the tight closure of the air ventilating opening 8 is improved.

In FIGS. 1 and 4 there can further be seen an annular seal 29 provided with a sealing lip. Such an annular seal 29 reliably provides for the free swivellability of the outer part 3 of the plug 2 on the inner part 4 without, detracting from a tight seal.

In FIG. 3, there is further shown recesses 30 on the circumference of the base member. These recesses 30 cooperate with corresponding protrusions, not shown in the drawing, provided on the inner circumference of the first coupling member 1 for locking the inner part 4 of the plug 2 against rotation, so that when rotating the outer part 3 by actuating the radial actuating protrusion 17 the inner part 4 reliably remains in its rotated position for assuring free flow through the flow passages in the operating position.

What is claimed is:

1. In a coupling having a longitudinally extending axis for connecting hose conduits for medical purposes including a first coupling member, a second coupling member releasably connected to said first coupling member, second hose connecting means for connecting said first and second coupling members to a second hose length, a sponge member soaked with a disinfectant within said first coupling member, a diaphragm connected within said second coupling member, and a hollow plug axially movable within said coupling members and extending in the operating position thereof through said sponge member and piercing through said diaphragm for coupling a first hose length to said second hose length through said coupling, the improvement comprising:

said second hose connecting means being on said second coupling member;

means for supporting said hollow plug on said first coupling member for relative axial movement therein;

said hollow plug comprising an outer part and an inner part telescopically and rotatably disposed within and relatively to said outer part; cooperating sealing means on said inner and outer parts for sealing said inner and outer parts with respect to each other;

a plurality of axially extending channels on said inner part;

at least one radial perforation in said inner part extending radially relative to and communicating with said axially extending channels;

first hose connecting means for said first hose length on said inner part and communicating with said at least one radial perforation; and radially extending openings in said outer part, said radial openings being closed by said inner part when said outer part is in a first relative rotated position with respect to said inner part, and in communication with said channels and said at least one radial perforation through said channels when said outer part is in a second position of rotation with respect to said inner part.

2. A coupling as claimed in claim 1 and further comprising:

a sealing disc mounted in said second coupling member for sealing engagement with said outer part of said plug when said plug is moved axially through said second coupling member.

3. A coupling as claimed in claim 1 and further comprising:

a further diaphragm perforatable by said plug mounted in said second coupling member for sealing engagement with said outer part of said plug when said plug is moved axially through said second coupling member.

4. A coupling as claimed in claim 1 and further comprising:

a guide slot in said first coupling member having a first part extending longitudinally and substantially parallel to said longitudinal axis from a proximal end remote from said diaphragm to a distal end, and a second part extending circumferentially from said distal end of said first part of said guide slot; and an actuating protrusion extending radially from said outer part of said plug through said guide slot for sliding engagement therein so that said protrusion is manipulable for moving said plug axially in said first part of said slot in said coupling member and rotatably in said second part for rotating said outer part between the closed position of said radial openings and said position in communication with said channels in said inner part.

5. A coupling as claimed in claim 1 and further comprising:

said second host connecting means on said second coupling member comprising a connecting element positioned eccentrically relative to said longitudinal axis;

a vent opening in said second coupling member located coaxially with said longitudinal axis; and means on said outer part of said plug engageable with said vent opening for closing said vent opening when said plug is moved axially through said sponge member and diaphragm in the coupled position for use.

6. A coupling as claimed in claim 5 wherein:

said means for closing said vent opening comprises a sealing protrusion on said one end of said outer part of said plug engageable in sealing relationship within said vent opening.

7. A coupling as claimed in claim 1 and further comprising:

a base disc on one end of said outer part of said plug adjacent said first hose connecting means; and claw member on said inner part of said plug adjacent said first hose connecting means engageable with said base disc for retaining said inner part in said outer part.

8. A coupling as claimed in claim 7 and further comprising;

a hollow conical sealing surface on said outer part extending through said base disc on said outer part;

said claw members being circumferentially spaced radially outwardly relative to said longitudinal axis; and a cooperating conical sealing surface on said inner part adjacent to and radially inwardly of said claw members for sealing engagement with said hollow conical sealing surface on said outer part when said inner and outer parts are connected together.

9. A coupling as claimed in claim 8 and further comprising:

an annular lip sealing means interposed between said inner part and said outer part adjacent said conical sealing surfaces.

10. A coupling as claimed in claim 1 and further comprising means for supporting said inner part of said plug within said outer part of said plug so that said outer part and inner part are axially moveable together and rotatably movable with respect to each other.

11. A coupling as claimed in claim 10 and further comprising:

at least one absorbing insert member in the form of an annular disc of foamed material within said second coupling part for engagement with said plug when said plug is moved axially through said diaphragm and sponge member for functioning as a stripping disc for wiping off and absorbing disinfectant material on the other surface of said plug.

12. A coupling as claimed in claim 11 and further comprising:

said second hose connecting means on said second coupling member comprising a connecting element positioned eccentrically relative to said longitudinal axis;

a vent opening in said second coupling member located coaxially with said longitudinal axis; and means on said outer part of said plug engageable with said vent opening for closing said vent opening when said plug is moved axially through said sponge member and diaphragm in the coupled position for use.

13. A coupling as claimed in claim 10 and further comprising:

said second host connecting means on said second coupling member comprising a connecting element positioned eccentrically relative to said longitudinal axis;

a vent opening in said second coupling member located coaxially with said longitudinal axis; and means on said outer part of said plug engageable with said vent opening for closing said vent opening when said plug is moved axially through said sponge member and diaphragm in the coupled position for use.

14. A coupling as claimed in claim 1 and further comprising:

at least one absorbing insert member in the form of an annular disc of foamed material within said second coupling part for engagement with said plug when said plug is moved axially through said diaphragm and sponge member for functioning as a stripping disc for wiping off and absorbing disinfectant material on the outer surface of said plug.

15. A coupling as claimed in claim 14 and further comprising:

said second hose connecting means on said second coupling member comprising a connecting element positioned eccentrically relative to said longitudinal axis;

a vent opening in said second coupling member located coaxially with said longitudinal axis; and means on said outer part of said plug engageable with said vent opening for closing said vent opening when said plug is moved axially through said sponge member and diaphragm in the coupled position for use.

16. A coupling as claimed in claim 15 and further comprising a separate mounting member insertable within said second coupling member for supporting said diaphragm and the stripper disc within said second coupling member.

17. A coupling as claimed in claim 14 and further comprising:

a further diaphragm perforatable by said plug mounted in said second coupling member for sealing engagement with said outer part of said plug when said plug is moved axially through said second coupling member.

18. A coupling as claimed in claim 17 and further comprising:

a base disc on one end of said outer part of said plug adjacent said first hose connecting means; and claw members on said inner part of said plug adjacent said first hose connecting means engageable with said base disc for retaining said inner part in said outer part.

19. A coupling as claimed in claim 14 and further comprising:

a sealing disc mounted in said second coupling member for sealing engagement with said outer part of said plug when said plug is moved axially through said second coupling member.

20. A coupling as claimed in claim 14 and further comprising a separate mounting member insertable within said second coupling member for supporting said diaphragm and the stripper disc within said second coupling member.

* * * * *